(12) United States Patent
Potter et al.

(10) Patent No.: US 8,236,827 B2
(45) Date of Patent: Aug. 7, 2012

(54) COMPOUNDS

(75) Inventors: Gerard Andrew Potter, Leicester (GB); Philip Huxley, Freeland (GB); Kenneth James Beresford, Bedford (GB)

(73) Assignee: Spear Therapeutics Limited, Leicester (GB)

( * ) Notice: Subject to any disclaimer, the term of this patent is extended or adjusted under 35 U.S.C. 154(b) by 347 days.

(21) Appl. No.: 12/478,587

(22) Filed: Jun. 4, 2009

(65) Prior Publication Data

US 2010/0168180 A1 Jul. 1, 2010

(51) Int. Cl.
*A01N 43/40* (2006.01)
*A61K 31/44* (2006.01)
*C07D 405/00* (2006.01)

(52) U.S. Cl. ............... 514/350; 514/338; 546/283.7

(58) Field of Classification Search ............ 514/350, 514/338; 546/283.7
See application file for complete search history.

(56) References Cited

U.S. PATENT DOCUMENTS

2007/0072833 A1 3/2007 Wendt et al.

FOREIGN PATENT DOCUMENTS

| WO | WO-03/028713 A | 4/2003 |
|---|---|---|
| WO | WO-2008/133955 A1 | 11/2008 |

OTHER PUBLICATIONS

Vippagunta et al. Advanced Drug Delivery Reviews, 2001, vol. 48, pp. 3-26.*
Bruno; Njar, "Targeting Cytochrome P450 Enzymes: A New Approach in Anti-Cancer Drug Development", *Bioorg. Med. Chem.*, 15:5047-5060 (2007).
Grosche et al., "Pyrazole, Pyridine and Pyridone Synthesis on Solid Support," *Synthesis*, 11:1961-1970 (1999).
Katritzky et al. "Solid-Phase Synthesis of 4,6-Disubstituted and 3,4,6-Trisubstituted Pyrid-2-Ones", *J. Comb. Chem.* 4(4):249-250 (2002).

Paluchowska et al., "Substitution Mode of the Amide Fragment in some New N-{ω-[4-(2-Methoxyphenyl)Piperazin-1-yl]Alkyl}Pyrid-2(1H)-Ones and their 5-HT$_{1A}$/5-HT$_{2A}$ Activity", *Polish Journal of Pharmacology*, 53:369-376 (2001).

\* cited by examiner

*Primary Examiner* — Samira Jean-Louis
(74) *Attorney, Agent, or Firm* — Mintz Levin Cohn Ferris Glovsky and Popeo, P.C.; Jennifer L. Loebach; Yongjun Zhang (57) ABSTRACT

A compound for use in the treatment of proliferative disorders, such as cancer, having the following formula:

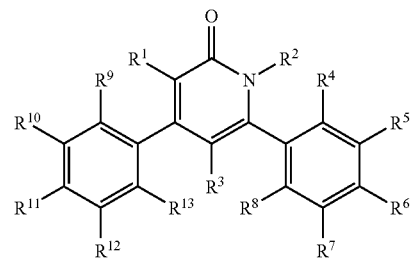

wherein:
$R^1$, $R^2$ and $R^3$ are independently H or lower alkyl;
$R^4$, $R^5$, $R^6$, $R^7$ and $R^8$ are independently H, halo, lower alkyl or —O-lower alkyl, provided that at least one is —O-lower alkyl; or at least one pair of $R^4$ to $R^8$, the members of which pair are adjacent to one another on the ring, are conjoined to form —O—$(CR^{14}R^{15})_n$—O—, where n is 1 or 2 and $R^{14}$ and $R^{15}$ are independently H or lower alkyl, and the remainder of $R^4$ to $R^8$ are independently H, halo, lower alkyl or —O-lower alkyl; and
$R^9$, $R^{10}$, $R^{11}$, $R^{12}$ and $R^{13}$ are independently H, halo, lower alkyl or —O— lower alkyl, provided that at least one is —O-lower alkyl; or at least one pair of $R^9$ to $R^{13}$, the members of which pair are adjacent to one another on the ring, are conjoined to form —O—$(CR^{16}R^{17})_m$—O—, where m is 1 or 2 and $R^{16}$ and $R^{17}$ are independently H or lower alkyl, and the remainder of $R^9$ to $R^{13}$ are independently H, halo, lower alkyl or —O-lower alkyl.

8 Claims, 3 Drawing Sheets

Tumor wet weight (grams)

COMPOUNDS

This application claims priority to United Kingdom patent application number GB 0810228.7 filed 4 Jun. 2008 the contents of which are incorporated herein by reference in their entirety.

TECHNICAL FIELD

The present invention relates to novel compounds for use in the treatment or prophylaxis of cancers and other proliferative conditions that are characterised by cells which express cytochrome P-450 CYP1B1. The present invention also provides pharmaceutical compositions comprising one or more such compounds for use in the treatment or prophylaxis of such cancers or other proliferative conditions, as well as methods for treating such cancers or other conditions in human or non-human animal patients.

BACKGROUND

Cytochrome P-450 CYP1B1 is a dioxin-inducible form of the cytochrome P-450 family of xenobiotic metabolising enzymes. CYP1B1 is expressed at a high frequency in a wide range of human cancers of different histogenetic types and is not expressed (or only at negligible levels) in normal tissues, see, e.g.: McFadyen M C, Melvin W T and Murray G I, "Cytochrome P450 Enzymes: Novel Options for Cancer Therapeutics", *Mol Cancer Ther.*, 3(3): 363-71, 2004; McFadyen M C and Murray G I, "Cytochrome P450 1B1: a Novel Anticancer Therapeutic Target", *Future Oncol.*, 1(2): 259-63, 2005; Sissung T M, Price D K, Sparreboom A and Figg W D, "Pharmacogenetics and Regulation of Human Cytochrome P450 1B1: Implications in Hormone-Mediated Tumor Metabolism and a Novel Target for Therapeutic Intervention", *Mol. Cancer. Res.*, 4(3): 135-50, 2006. More specifically, CYP1B1 has been shown to be expressed in bladder, brain, breast, colon, head and neck, kidney, lung, liver, ovarian, prostate and skin cancers, without being expressed in the corresponding normal tissue.

For example, Barnett, et al., in *Clin. Cancer Res.*, 13(12): 3559-67, 2007, reported that CYP1B1 was over-expressed in glial tumours, including glioblastomas, anaplastic astrocytomas, oligodendrogliomas and anaplastic oligodendrogliomas, but not unaffected brain tissue.

Carnell, et al., in *Int. J. Radiat. Oncol. Biol. Phys.*, 58(2): 500-9, 2004, reported that CYP1B1 was over-expressed in prostate adenonocarcinomas, but not in matched normal prostate tissue.

Carnell et al., 2004 (ibid.) also showed that CYP1B1 is expressed in (n=22, 100%) of bladder carcinomas Downie, et al., in *Clin. Cancer Res.*, 11(20): 7369-75, 2005 and McFadyen, et al., in *Br. J. Cancer*, 85(2): 242-6, 2001, reported increased expression of CYP1B1 in primary and metastatic ovarian cancer, but not in normal ovary tissue.

Gibson, et al., in *Mol. Cancer. Ther.*, 2(6): 527-34, 2003, and Kumarakulasingham, et al., in *Clin. Cancer Res.*, 11(10): 3758-65, 2005, reported that CYP1B1 was over-expressed in colon adenocarcionomas as compared to matched normal tissue.

Several studies have shown that CYP1B1 is over-expressed in breast cancer as compared to matched normal tissue. (See, e.g.: Murray G I, Taylor M C, McFadyen M C, McKay J A, Greenlee W F, Burke M D and Melvin W T, "Tumor-Specific Expression of Cytochrome P450 CYP1B1", *Cancer Res.*, 57(14): 3026-31, 1997; Haas S, Pierl C, Harth V, Pesch B, Rabstein S, Bruning T, Ko Y, Hamann U, Justenhoven C, Brauch H and Fischer H P, "Expression of Xenobiotic and Steroid Hormone Metabolizing Enzymes in Human Breast Carcinomas". *Int. J. Cancer*, 119(8): 1785-91, 2006; McKay J A, Murray G I, Ah-See A K, Greenlee W F, Marcus C B, Burke M D and Melvin W T, "Differential Expression of CYP1A1 and CYP1B1 in Human Breast Cancer", *Biochem. Soc. Trans.*, 24(2): 327S, 1996).

Everett, et al., in *J. Clin. Oncology*, 25: 18S, 2007, reported that CYP1B1 was over-expressed in malignant melanoma and disseminated disease but not in normal skin.

Gibson, et al., 2003 (ibid.) and Chang, et al., in *Toxicol. Sci.*, 71(1): 11-9, 2003, both reported that while CYP1B1 was not present in normal liver it was over-expressed in stage IV metastasis to the liver.

Greer, et al., in *Proc. Am. Assoc. Cancer Res.*, 45: 3701, 2004, reported that CYP1B1 was over-expressed during the malignant progression of head and neck squamous cell carcinoma but not in normal epithelium.

McFadyen, et al., in Br. J. Cancer, 91(5): 966-71, 2004, detected CYP1B1 in renal carcinomas but not in corresponding normal tissue.

Murray, et al., 2004 (ibid.) used immunohistochemistry to show over-expression of CYP1B1 in lung cancer cells as compared to normal lung tissue.

It is evident from the numerous disclosures cited above that CYP1B1 expression is characteristic of a range of different cancers and other proliferative conditions, and that CYP1B1 expression may be used to define such a range of cancers and other conditions. As normal (non-cancerous) cells do not express significant levels of CYP1B1, it may also be reasonably expected that compounds that exhibit cytotoxicity in cells expressing CYP1B1, but are substantially non-cytotoxic in normal cells, would have utility as targeted anti-cancer agents in cancers characterised by CYP1B1 expression. By "targeted" is meant that such compounds could be delivered systemically and would only be activated in the presence of cancerous cells expressing CYP1B1, remaining substantially non-toxic to the rest of the body.

Further, a number of cytochrome P450 enzymes are known to metabolise and detoxify a variety of anticancer drugs. McFadyen, et al. in Biochem Pharmacol. 2001, Jul. 15; 62(2): 207-12 demonstrated a significant decrease in the sensitivity of docetaxel in cells expressing CYP1B1 as compared with non-CYP1B1 expressing cells. This finding indicates that the presence of CYP1B1 in cells may decrease their sensitivity to some cytotoxic drugs. CYP1B1 activated pro-drugs may therefore be useful for the treatment of cancers whose drug resistance is mediated by CYP1B1.

WO-A-03/028713 discloses 3,4-methylenedioxy chalcones for use in the treatment of proliferative conditions, which 3,4-methylenedioxy chalcones exhibit such cytotoxicity in CYP1B1 expressing cells. According to WO-A-03/028713, such substituted chalcones may be represented by formula (A):

wherein:

each of $R^{B2}$, $R^{B3}$, $R^{B4}$ and $R^{B5}$ is independently —H, —OH or —OMe;

each of $R^1$ and $R^2$ is independently —H, optionally substituted $C_{1-4}$ alkyl or optionally substituted $C_{5-20}$ aryl;

$R^{A3}$ is —H, —OH, —OC(=O)$R^E$, —OS(=O)$_2$OH or —OP(=O)(OH)$_2$; and $R^E$ is —H, optionally substituted $C_{1-6}$ alkyl, optionally substituted $C_{3-20}$ heterocyclyl or optionally substituted $C_{5-20}$ aryl.

SUMMARY OF THE INVENTION

In one aspect, the invention relates, in part, to a compound of formula (I):

(I)

or a pharmaceutically acceptable salt, solvate, tautomer, amide, ester, ether, chemically protected form or prodrug thereof, wherein:

R1, R2 and R3 are independently H or lower alkyl;

R4, R5, R6, R7 and R8 are independently H, halo, lower alkyl or —O-lower alkyl, provided that at least one is —O-lower alkyl; or at least one pair of R4 to R8, the members of which pair are adjacent to one another on the ring, are conjoined to form —O—(CR14R15)n-O—, where n is 1 or 2 and R14 and R15 are independently H or lower alkyl, and the remainder of R4 to R8 are independently H, halo, lower alkyl or —O-lower alkyl; and R9, R10, R11, R12 and R13 are independently H, halo, lower alkyl or —O— lower alkyl, provided that at least one is —O-lower alkyl; or at least one pair of R9 to R13, the members of which pair are adjacent to one another on the ring, are conjoined to form —O—(CR16R17)m-O—, where m is 1 or 2 and R16 and R17 are independently H or lower alkyl, and the remainder of R9 to R13 are independently H, halo, lower alkyl or —O-lower alkyl.

For example, in a compound of formula I, R6 and R11 are not both —OMe.

For example, in a compound of formula I, R9, R12 and R13 are independently H, halo or lower alkyl, and R10 and R11 are conjoined to form —O—C(R16R17)m-O—, where m is preferably 1.

For example, in a compound of formula I, one of R9 to R13 is —O—R18, R18 is lower alkyl, and the remainder are independently H, halo or lower alkyl.

For example, in a compound of formula I, at least two of R4, R5, R6, R7 and R8 are —O-lower alkyl.

For example, in a compound of formula I, R6 is —O—R19, R19 is lower alkyl.

For example, a compound of the invention is:

(II)

(III)

(V)

or (VI)

In one aspect, the invention relates to a metabolite of a compound of formula I, wherein the metabolite is the product of said compound as a substrate for the CYP1B1 enzyme.

In another aspect, the invention relates, in part, to a cytotoxic compound having a formula (X):

(X)

or a pharmaceutically acceptable salt, solvate, tautomer, amide, ester, ether, chemically protected form or prodrug thereof, wherein:

R1-R3 are independently H or lower alkyl; and

R4-R13 are independently H, OH, halo, lower alkyl or —O-lower alkyl, provided that at least one of $R^4$-$R^{13}$ is OH.

For example, in the cytotoxic compound of formula X, when R6 is Cl then R12 is not OH or OMe; or when $R^5$ is OMe then $R^{12}$ is not OH, or when $R^6$ is OH then $R^{11}$ is not OMe.

For example, in the cytotoxic compound of formula X, at least two of R4 to R13 are OH.

For example, in the cytotoxic compound of formula X, at least two of R9 to R13 are OH.

For example, in the cytotoxic compound of formula X, when R5 is OH or —O— lower alkyl and R6 is OH or —O-lower alkyl.

For example, in the cytotoxic compound of formula X, two of R9 to R13 are OH, with the remainder being H, halo, or lower alkyl.

For example, the cytotoxic compound of formula X is:

(XI)

(XIIa)

(XIIb)

(XIIIa)

(XIIIb)

(XIVa)

or (XIVb)

In another aspect, the invention relates to a method of treating a proliferative disorder by administering to a human or non-human animal, in need thereof, a therapeutically effective amount of a compound of group A or group B, wherein said group A is a compound of formula I:

(I)

wherein:
$R^1$, $R^2$ and $R^3$ are independently H or lower alkyl;
$R^4$, $R^5$, $R^6$, $R^7$ and $R^8$ are independently H, halo, lower alkyl or —O-lower alkyl, provided that at least one is —O-lower alkyl; or at least one pair of $R^4$ to $R^8$, the members of which pair are adjacent to one another on the ring, are conjoined to form —O—(CR$^{14}$R$^{15}$)$_n$—O—, where n is 1 or 2 and $R^{14}$ and $R^{15}$ are independently H or lower alkyl, and the remainder of $R^4$ to $R^8$ are independently H, halo, lower alkyl or —O-lower alkyl; and
$R^9$, $R^{10}$, $R^{11}$, $R^{12}$ and $R^{13}$ are independently H, halo, lower alkyl or —O— lower alkyl, provided that at least one is —O-lower alkyl; or at least one pair of $R^9$ to $R^{13}$, the members of which pair are adjacent to one another on the ring, are conjoined to form —O—(CR$^{16}$R$^{17}$)$_m$—O—, where m is 1 or 2 and $R^{16}$ and $R^{17}$ are independently H or lower alkyl, and the remainder of $R^9$ to $R^{13}$ are independently H, halo, lower alkyl or —O-lower alkyl;
and wherein said group B is a cytotoxic compound of formula X:

(X)

wherein:

$R^1$-$R^3$ are independently H or lower alkyl; and $R^4$-$R^{13}$ are independently H, OH, halo, lower alkyl or —O-lower alkyl, provided that at least one of $R^4$-$R^{13}$ is OH.

For example, the proliferative disorder is a cancer.

The cancer can be, for example, cancer of the lung, colon, breast, ovarian, prostate, liver, pancreas, brain, bladder, kidney or skin.

In one aspect the method of the invention includes administering to a human or non-human animal in need thereof a therapeutically effective amount of a cytotoxic compound of group B, wherein said cytotoxic compound is produced in the body.

In another aspect, the invention relates, in part, to a pharmaceutical composition comprising one or more compounds of formula I together with one or more pharmaceutically acceptable excipients.

DETAILED DESCRIPTION OF THE INVENTION

An object of the present invention is to provide alternative compounds that exhibit cytotoxicity in cancer cells, but not in normal cells.

Another object of the present invention is to provide alternative compounds that may suitably be used for the treatment or prophylaxis of cancers or other proliferative conditions.

Yet another object of the present invention is to provide compounds that may be used for the treatment or prophylaxis of cancers whose drug resistance is mediated by CYP1B1.

Yet another object of the present invention is to provide an alternative method of treating or preventing cancers or other proliferative conditions.

According to one aspect of the present invention therefore there are provided compounds represented by formula I:

(I)

wherein:

$R^1$, $R^2$ and $R^3$ are independently H or lower alkyl;

$R^4$, $R^5$, $R^6$, $R^7$ and $R^8$ are independently H, halo, lower alkyl or —O-lower alkyl, provided that at least one is —O-lower alkyl; or at least one pair of $R^4$ to $R^8$, the members of which pair are adjacent to one another on the ring, are conjoined to form —O—$(CR^{14}R^{15})_n$—O—, where n is 1 or 2 and $R^{14}$ and $R^{15}$ are independently H or lower alkyl, and the remainder of $R^4$ to $R^8$ are independently H, halo, lower alkyl or —O-lower alkyl; and $R^9$, $R^{10}$, $R^{11}$, $R^{12}$ and $R^{13}$ are independently H, halo, lower alkyl or —O— lower alkyl, provided that at least one is —O-lower alkyl; or at least one pair of $R^9$ to $R^{13}$, the members of which pair are adjacent to one another on the ring, are conjoined to form —O—$(CR^{16}R^{17})_m$—O—, where m is 1 or 2 and $R^{16}$ and $R^{17}$ are independently H or lower alkyl, and the remainder of $R^9$ to $R^{13}$ are independently H, halo, lower alkyl or —O-lower alkyl;

and a pharmaceutically acceptable salt, tautomer, solvate, amide, ester, ether, chemically protected form or prodrug thereof.

It has been found that compounds of the present invention exhibit cytotoxicity in cells expressing CYP1B1 enzyme, but are substantially non-toxic in normal cells that do not express CYP1B1. Compounds of the invention may also exhibit cytotoxicity in cells expressing CYP1A1 enzyme. In practice, therefore, the compounds of the invention are non-toxic prodrugs which are converted by CYP1B1 into cytotoxic agents.

Suitably, the compounds of the invention have an $IC_{50}$ value as defined below of less than 10 µM, advantageously less than 5 µM, and preferably less than 1.0 µM or 0.5 µM.

In some embodiments, the cytotoxicity of a compound of the invention may be measured by incubating the compound at different serial dilutions with cells engineered to express CYP1B1. Suitably, said cells may be Chinese Hamster Ovary (CHO) cells, which may contain recombinant CYP1B1 and cytochrome P-450 reductase (CPR). High levels of functional enzyme when co-expressed with human P-450 reductase may be achieved using dihydrofolate reductase (DHFR) gene amplification. Typically, the engineered cells may be incubated with the compound and, after a suitable period of time (e.g., 96 hours), further incubated (e.g., for 1.5 hours) with a suitable assay reagent to provide an indication of the number of living cells in culture. A suitable assay reagent is MTS (see below) which is bioreduced by cells into a formazan product that is soluble in tissue culture medium. The absorbance of the formazan product can be directly measured at 510 nm, and the quantitative formazan product as measured by the amount of absorbance at 490 nm or 510 nm is directly proportional to the number of living cells in culture. Detailed methods for determining the $IC_{50}$ value of a compound according to the invention are described in Example 1 below.

By way of comparison, the $IC_{50}$ values of the compounds of the invention may also be measured in cells (e.g., Chinese Hamster Ovary cells) that do not contain CYP1B1, for example wild type CHO cells. The compounds of the invention may suitably have a fold selectivity for CYP1B1 expressing cells of at least 20, where the "fold selectivity" is defined as the quotient of the $IC_{50}$ value of a given compound in non-CYP1 expressing cells and the $IC_{50}$ value of the same compound in CYP1B1 expressing cells.

As such, the present invention also comprehends the use of one or more of the compounds of the invention, including the aforementioned pharmaceutically acceptable salts, solvates and prodrugs, for use in the treatment of the human or animal body by therapy, particularly the treatment or prophylaxis of proliferative conditions such, for example, as proliferative disorders or diseases, in humans and non-human animals, including proliferative conditions which are characterised by cells that express CYP1B1. More particularly, the invention comprehends the use of one or more of the compounds of the invention for the treatment of cancers characterised by CYP1B1 expression.

According to another aspect of the present invention, therefore, there is provided a method of treatment or prophylaxis of a proliferative condition which comprises the administration to a human or non-human animal patient in need thereof of a therapeutically effective amount of at least one of the compounds of the present invention.

By "proliferative condition" herein is meant a disease or disorder that is characterised by an unwanted or uncontrolled cellular proliferation of excessive or abnormal cells which is undesired, such as, neoplastic or hyperplastic growth, whether in vitro or in vivo. Examples of proliferative conditions are pre-malignant and malignant cellular proliferation, including malignant neoplasms and tumours, cancers, leukemias, psoriasis, bone diseases, fibroproliferative disorders (e.g., of connective tissues) and atherosclerosis.

Said proliferative condition may be characterised by cells that express CYP1B1.

Said proliferative condition may be selected from bladder, brain, breast, colon, head and neck, kidney, lung, liver, ovarian, prostate and skin cancer. In some embodiments, said proliferative condition may comprise a solid tumour.

By "treatment" herein is meant the treatment by therapy, whether of a human or a non-human animal (e.g., in veterinary applications), in which some desired therapeutic effect on the proliferative condition is achieved; for example, the inhibition of the progress of the disorder, including a reduction in the rate of progress, a halt in the rate of progress, amelioration of the disorder or cure of the condition. Treatment as a prophylactic measure is also included. By a "therapeutically-effective amount" herein is meant an amount of the one or more compounds of the invention or a pharmaceutical formulation comprising such one or more compounds, which is effective for producing such a therapeutic effect, commensurate with a reasonable benefit/risk ratio.

The compounds of the present invention may therefore be used as anticancer agents. By the term "anticancer agent" herein is meant a compound which treats a cancer (i.e., a compound that is useful in the treatment of a cancer). The anti-cancer effect of the compounds of the invention may arise through one or more mechanisms, including the regulation of cell proliferation, the inhibition of angiogenesis, the inhibition of metastasis, the inhibition of invasion or the promotion of apoptosis.

It will be appreciated that appropriate dosages of the compounds of the invention may vary from patient to patient. Determining the optimal dosage will generally involve the balancing of the level of therapeutic benefit against any risk or deleterious side effects of the treatments of the present invention. The selected dosage level will depend on a variety of factors including the activity of the particular compound, the route of administration, the time of administration, the rate of excretion of the compound, the duration of the treatment, other drugs, compounds or materials used in combination and the age, sex, weight, condition, general health and prior medical history of the patient. The amount of compound(s) and route of administration will ultimately be at the discretion of the physician, although generally the dosage will be to achieve local concentrations at the site of action which achieve the desired effect.

Administration in vivo can be effected in one dose, continuously or intermittently throughout the course of treatment. Methods of determining the most effective means and dosage of administration are well known to a person skilled in the art and will vary with the formulation used for therapy, the purpose of the therapy, the target cell being treated, and the subject being treated. Single or multiple administrations can be carried out with the dose level and pattern being selected by the treating physician.

In general, a suitable dose of the one or more compounds of the invention may be in the range of about 1 µg to about 5000 µg/kg body weight of the subject per day, e.g., 1, 5, 10, 25, 50, 100, 250, 1000, 2500 or 5000 µg/kg per day. Where the compound(s) is a salt, solvate, prodrug or the like, the amount administered may be calculated on the basis of the parent compound and so the actual weight to be used may be increased proportionately.

In some embodiments, the one or more compounds of the present invention may be used in combination therapies for the treatment of proliferative conditions of the kind described above, i.e., in conjunction with other agents, for example, cytotoxic agents.

In some embodiments, $R^9$, $R^{12}$ and $R^{13}$ of formula I above may independently be H, halo or lower alkyl, and $R^{10}$ and $R^{11}$ may be conjoined to form —O—C($R^{16}R^{17}$)$_m$—O—. m is preferably 1. Suitably, $R^9$, $R^{12}$ and $R^{13}$ may be H. $R^{16}$ and $R^{17}$ may both be H. Thus in some embodiments, the compounds of the invention may be represented by formula Ia:

(Ia)

Alternatively, one of $R^9$ to $R^{13}$ may be —O—$R^{18}$, $R^{18}$ being lower alkyl, and the remainder being independently H, halo or lower alkyl. For instance, $R^{18}$ may be $C_{1-4}$ or $C_{1-3}$ alkyl, preferably n-propyl. In such case, one of $R^{10}$ to $R^{12}$ may be —O—$R^{18}$, preferably $R^{11}$; and said remainder of $R^9$ to $R^{13}$ may be H. Thus in some embodiments, the compounds of the invention may be represented by formula Ib:

(Ib)

By "lower alkyl" herein is meant a $C_{1-6}$ alkyl group, preferably $C_{1-4}$ or $C_{1-3}$. Such lower alkyl moiety may be straight chain or branched. Said lower alkyl group may be and substituted, or maybe substituted with one or more halo moieties. For instance, a methyl group may be substituted with one or more fluoro radicals.

By "halo" herein is meant fluoro-, chloro-, bromo- or iodo-, preferably fluoro.

Suitably, one or two of $R^4$, $R^5$, $R^6$, $R^7$ and $R^8$ may be —O-lower alkyl. Such compounds have been found to be particularly cytotoxic in cells expressing CYP1B1.

Thus, in some embodiments $R^4$ and $R^6$ or $R^5$ and $R^6$ may be —O—$R^{19}$, $R^{19}$ being lower alkyl, and the remainder may be independently H, halo or lower alkyl.

In some preferred embodiments, $R^5$ and $R^6$ may be —O—$R^{19}$, $R^4$, $R^7$ and $R^8$ may independently be H, halo or lower alkyl, $R^9$, $R^{12}$ and $R^{13}$ may independently be H, halo or lower alkyl, and $R^{10}$ and $R^{11}$ may be conjoined to form —O—C($R^{16}R^{17}$)$_m$—O—, where m is preferably 1. Accordingly, the compounds of the invention may be represented by the formula Ia':

(Ia')

Alternatively, $R^6$ may be —O—$R^{19}$, and the remainder of $R^4$, $R^5$, $R^7$ and $R^8$ may be independently H, halo or lower alkyl.

Suitably, $R^{19}$ may be $C_{1-4}$ or $C_{1-3}$ alkyl, preferably methyl. Further, the remainder of $R^4$ to $R^8$ maybe H.

By way of example, a compound in accordance with the invention may be represented by formula II:

(II)

Further examples of compounds in accordance with the invention are represented by the formulae III, IV, V and VI:

(III)

(V)

(VI)

As mentioned above, the compounds of the invention include the pharmaceutically acceptable salts and solvates of formula I.

Examples of pharmaceutically acceptable salts are discussed in Berge, et al., 1977, "Pharmaceutically Acceptable Salts," *J. Pharm. Sci.*, Vol. 66, pp. 1-19, the contents of which are incorporated herein by reference.

The term "solvate" is used herein in the conventional sense to mean a complex of a compound of formula I and a solvent. If the solvent is water, then the solvate may be conveniently referred to as a hydrate, for example, a mono-hydrate, a di-hydrate, a tri-hydrate, etc.

The present invention also comprehends the use of one or more of the compounds of the invention in the manufacture of a pharmaceutical formulation for use in the treatment of a proliferative condition, particularly such a disorder or disease which is characterised by the expression of CYP1B1 in cells, especially a solid tumour or cancer, including the cancers mentioned above.

Accordingly, in yet another aspect of the present invention there is provided such a pharmaceutical formulation comprising one or more of the compounds of the invention together with one or more optional pharmaceutically acceptable excipients.

By "pharmaceutically acceptable excipients" herein is meant pharmaceutical excipients that are suitable for use in contact with the tissues of the patient without excessive toxicity, irritation, allergic response or other problem or complication, commensurate with a reasonable benefit/risk ratio. Each excipient must also be "acceptable" in the sense of being compatible with the other ingredients of the formulation.

Suitably, the composition of the invention may be formulated as a unit dosage form. Each unit dosage form may comprise all or a predetermined fraction of the daily dose amount of the one or more compounds of the invention, e.g., one half or one quarter of the daily dose amount.

Thus, the composition may be formulated as a tablet, a pill, a capsule, a powder, granules, a sterile parenteral solution or suspension, a metered aerosol or liquid spray, drops, an ampoule, an auto-injector device, a suppository, a cream or a gel. Said composition may be adapted for oral, enteral parenteral, intrathecal, intranasal, sublingual, rectal or topical administration, or for administration by inhalation or insufflation. Oral compositions such as tablets, pills, capsules or wafers are particularly preferred.

For preparing a solid dosage form such as a tablet, said one or more compounds may be mixed with one or more pharmaceutical excipients, e.g., conventional tabletting ingredients such as corn starch, lactose, sucrose, sorbitol, talc, stearic acid, magnesium stearate, dicalcium phosphate or gums, or other pharmaceutical diluents, e.g., water, to form a solid pre-formulation composition containing a substantially homogeneous mixture of said one or more compounds, such that said one or more compounds are dispersed evenly throughout the composition, so that the composition may be readily subdivided into equally effective unit dosage forms such as tablets, pills and capsules.

Said solid pre-formulation composition may then be subdivided into unit dosage forms of the kind mentioned above which may each contain from 0.1 to about 500 mg of the one or more compounds. Favoured unit dosage forms contain from 1 to 500 mg, e.g., 1, 5, 10, 25, 50, 100, 300 or 500 mg, of the compound(s).

When formulated as a tablet or pill, said tablet or pill may be coated or otherwise compounded to provide a dosage form affording the advantage of prolonged action. For instance, said tablet or pill can comprise an inner dosage and an outer dosage component, the latter being in the form of an envelope over the former. These two components may be separated by an enteric layer that serves to resist disintegration in the stomach and permits the inner component to pass intact into the duodenum or to be delayed in release. A variety of materials are known in the use in such enteric layers or coatings, such materials including a number of polymeric acids and mixtures of polymeric acids with such materials as shellac, cetyl alcohol and cellulose acetate.

Alternatively, the pharmaceutical composition of the present invention may be formulated as a liquid dosage form for administration orally or by injection; for example an aqueous solution, a suitably flavoured syrup, an aqueous or oil suspension or a flavoured emulsion with edible oils such, for example, as cottonseed oil, sesame oil, coconut oil or peanut oil, as well as an elixir or a similar pharmaceutical vehicle. Suitable dispersing or suspending agents for an aqueous suspension include synthetic and natural gums, e.g., tragacanth, acacia, alginate, dextran, sodium carboxymethylcellulose, methylcellulose, polyvinyl-pyrrolidone or gelatin.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect.

As mentioned above, the compounds of the present invention have been found to be substantially non-cytotoxic in cells that do not express CYP1B1 enzyme. Without wishing to be bound by theory, it is believed that compounds of the present invention are converted by CYP1B1 in cells that express the same to active metabolites that are cytotoxic. Experimental data indicates that such active cytotoxic compounds are broad-spectrum kinase inhibitors that are generally cytotoxic in animal cells irrespective of CYP1B1 expression. It is thought that it is the conversion of the compounds of the invention by CYP1B1 in cells expressing the same from non-cytotoxic precursors to active cytotoxic compounds that renders the compounds of the invention suitable for use as targeted anti-cancer agents for the treatment or prophylaxis of proliferative conditions characterised by CYP1B1 expression.

In yet another aspect of the present invention therefore there are provided the cytotoxic compounds of the present invention, which cytotoxic compounds are the products of catalytic activity of the CYP1B1 enzyme on the compounds of the invention. The catalytic activity of the CYP1B1 enzyme is understood to involve two different mechanisms 1) de-alkylation or 2) hydroxylation. The present invention therefore comprehends de-alkylated or hydroxylated forms of the compounds of the invention.

In some embodiments, the cytotoxic compounds of the present invention may be represented by formula X:

(X)

wherein:

$R^1$-$R^3$ are independently H or lower alkyl;

$R^4$-$R^{13}$ are independently H, OH, halo, lower alkyl or —O— lower alkyl, provided that at least one of $R^4$-$R^{13}$ is OH;

and pharmaceutically acceptable salt, solvate, amide, ester, ether, chemically protected form or prodrug thereof.

Preferably at least two of $R^4$ to $R^{13}$ is OH.

In some embodiments $R^4$, $R^7$ and $R^8$ are H, and preferably $R^9$, $R^{12}$ and $R^{13}$ are H.

In some further preferred embodiments at least two of $R^4$ to $R^8$ are —O— lower alky, and preferably at least two of $R^9$ to $R^{13}$ are OH.

Alternatively, $R^5$ is OH or —O— lower alkyl and $R^6$ is OH or —O— lower alkyl, and preferably at least two of $R^9$ to $R^{13}$ are OH. Further $R^{10}$ and $R^{11}$ are OH and the remainder may be H.

In a further embodiment, when $R^5$ is OH or —O— lower alkyl and $R^6$ is OH or —O— lower alkyl, at least one of $R^9$ to $R^{12}$ is —O— lower alkyl and preferably $R^{11}$ is —O— lower alkyl.

In another embodiment, when $R^5$ is OH or —O— lower alkyl and $R^6$ is OH or —O— lower alkyl, $R^{11}$ is OH and the remainder are H.

At least one of $R^4$ to $R^8$ may be OH and at least one of $R^9$ to $R^{13}$ may be —O-lower alkyl, the remainder of $R^4$ to $R^{13}$ being independently H, halo, lower alkyl or —O-lower alkyl.

In some embodiments, two of $R^4$ to $R^8$ may be OH, with the remainder being H, halo, or lower alkyl, preferably H. Said two of $R^4$ to $R^8$ may be adjacent to one another on the ring. One of $R^9$ to $R^{13}$ may be —O—$R^{18}$, $R^{18}$ being H, OH, lower alkyl as described above, the remainder being independently H, halo or lower alkyl. In such case, one of $R^{10}$ to $R^{12}$ may be —O—$R^{18}$, preferably $R^{11}$; and said remainder of $R^9$ to $R^{13}$ may be H.

Alternatively, at least one of $R^9$ to $R^{13}$ may be OH and at least one of $R^4$ to $R^8$ may be —O-lower alkyl, the remainder of $R^4$ to $R^{13}$ being independently be H, halo, lower alkyl or —O-lower alkyl.

In some embodiments, two of $R^9$ to $R^{13}$ may be OH, with the remainder being H, halo, or lower alkyl, preferably H. Said two of $R^9$ to $R^{13}$ may be adjacent to one another on the ring. Thus, $R^9$, $R^{12}$ and $R^{13}$ may independently be H, halo or lower alkyl, and $R^{10}$ and $R^{11}$ may both be OH. Suitably, $R^9$, $R^{12}$ and $R^{13}$ may be H. Further, one or two of $R^4$, $R^5$, $R^6$, $R^7$ and $R^8$ may be —O-lower alkyl. Thus, in some embodiments $R^4$ and $R^6$ or $R^5$ and $R^6$ may be —O—$R^{19}$, $R^{19}$ being lower alkyl as described above, and the remainder may be independently H, halo or lower alkyl.

In some preferred embodiments, $R^5$ and $R^6$ may be —O—$R^{19}$, $R^4$, $R^7$ and $R^8$ being independently H, halo or lower alkyl; $R^9$, $R^{12}$ and $R^{13}$ may independently be H, halo or lower alkyl, and $R^{10}$ and $R^{11}$ may both be OH.

Alternatively, $R^6$ may be —O—$R^{19}$ and the remainder of $R^4$, $R^5$, $R^7$ and $R^8$ may be independently H, halo or lower alkyl.

The remainder of $R^4$ to $R^8$ maybe H.

By way of example, a cytotoxic compounds according to the invention may be represented by formulae XI, XII, XIII and XIV:

(XI)

(XIIa)

(XIIb)

(XIIIa)

(XIIIb)

(XIVa)

or (XIVb)

It will be appreciated that all tautomers of shown or described compounds are also considered to be part of the present invention. Furthermore, the invention also includes metabolites of the compounds described herein.

"Tautomers" refers to compounds whose structures differ markedly in arrangement of atoms, but which exist in easy and rapid equilibrium. It is to be understood that compounds of Formula I may be depicted as different tautomers. It should also be understood that when compounds have tautomeric forms, all tautomeric forms are intended to be within the scope of the invention, and the naming of the compounds does not exclude any tautomer form.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds

A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g. in the nucleobases guanine, thymine, and cytosine), amine-enamine and enamine-enamine. An example of a tautomer of the invention is:

It will further be appreciated that all showing or described compounds, including intermediates, including protecting groups are also to be part of the invention. "Protecting group" refers to a grouping of atoms that when attached to a reactive group in a molecule masks, reduces or prevents that reactivity. When a protecting group is attached to a molecule it forms a chemically protected form of the compound. Examples of protecting groups can be found in Green and Wuts, *Protective Groups in Organic Chemistry*, (Wiley, $2^{nd}$ ed. 1991); Harrison and Harrison et al., *Compendium of Synthetic Organic Methods*, Vols. 1-8 (John Wiley and Sons, 1971-1996); and Kocienski, *Protecting Groups*, (Verlag, $3^{rd}$ ed. 2003).

Furthermore, all shown or described compounds, including intermediates, including an amine protecting groups are considered to be part of the invention. The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butdyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other suitable amine protecting groups are straightforwardly identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Synthesis 1: Compound V

Compound V

Step-1

To 4-dihydroxybenzaldehyde (5 g) in DMF (50 ml); K₂CO₃ (7.5 g), diiodomethane (12.5 g) were added and the reaction mixture was refluxed for 2 hrs at temperature 110° C. Progress of the reaction was monitored by TLC. When the reaction was complete the mixture was cooled to room temperature, filtered through a Celite bed and washed with DCM. Water (100 ml) was added to the filtrate and the compound was extracted with DCM (3×200 ml). Combined extracts were washed with water, dried over Na₂SO₄ and concentrated under reduced pressure. The crude compound was purified by column chromatography (silica gel, 10% EtOAc/hexane) to yield intermediate 1.

Step-2

To (2,4-dihydroxyphenyl)ethanone (10 g) in acetone (100 ml); K₂CO₃ (45 g), DMSO₄ (20.7 g) were added and the reaction mixture was stirred overnight at 65-70° C. Progress of the reaction was monitored by TLC. When the reaction was complete the mixture was filtered through a Celite bed and washed with acetone (150 ml). Filtrate was concentrated under reduced pressure, residue obtained was taken in water (50 ml) and the compound extracted with DCM (2×100 ml). Combined extracts were dried over Na₂SO₄, concentrated under reduced pressure and the crude extract purified by column chromatography (silica gel, 10% EtOAc/hexane) to yield the unstable intermediate 2.

Step-3

In a (250 ml) single neck RB flask piperonal (3 g) and 3,4-dimethoxy-acetophenone (3.6 g) were taken and dissolved in MeOH (45 ml) and cooled to 0-10° C. 50% NaOH solution (24 ml) was added and stirred for 2 hr at room temperature. Solid was filtered and washed with water. Solid was dried at 60° C. for 1 hr to yield intermediate 3.

Step-4

In a (100 ml) single neck RB flask 3 (2 g), N-acetyl glycine amide (1 g), Cs₂CO₃ (2.75 g) were dissolved in DMF (20 ml) and heated to 140-150° C. for 1½ hr and cooled to 0-10° C. 10% HCl solution (20 ml) (pH=1) was added and the reaction mixture kept aside for 4-5 hr. Solid was thrown out and washed with hexane. The compound was dried at 60° C. for 5 hr to yield 800 mgs of 96% pure product (a cream yellow colored solid).

Syntheses 2 and 3: Compounds II, III and VI

Compound II, III and Compound VI were synthesised using methods directly analogous to those used for the synthesis of Compound V above.

Synthesis 4: Compound XI

Compound X

Step 1
(Set up a 250 ml SN RB flask equipped with Guard tube).
Pyridinium P-toluenesulfonate (catalytic) and DHP (9.23 g) were added to dihydroxybenzaldehyde (5 g) in DCM (50 ml) at room temperature. The reaction mixture was allowed to stir at room temperature over night. Progress of the reaction was monitored by TLC. Along with some starting material, mono protected compound was also observed. To DCM layer water washes (2×100 ml) were given, dried over $Na_2SO_4$ and distilled on rotavapour to obtain crude product which was purified by column chromatography (with basic $SiO_2$ & 5-8% EtOAc/hexane).

Step-2
(Set up a SN RB flask equipped with Guard tube).
To 4 (3 g) in methanol (30 ml); barium hydroxide (5.522 g) and di-methoxy acetophenone (1.7532 g) were added at room temperature. Reaction mixture was allowed to stir at room temperature over night. Progress of the reaction was monitored by TLC. Reaction mixture was quenched with 2N HCl at 0° C. Methanol was distilled, compound was taken in ethyl acetate and water washes (3×100 ml) were given. The ethyl acetate layer was separated out and dried over $Na_2SO_4$. Ethyl acetate was distilled on rotavapour and product was purified by column chromatography (with basic $SiO_2$ & 23% EtOAc/hexane).

Step 3:
(Set up a SN RB flask equipped with Guard tube and Reflux condenser).
To 5 (1 g) in DMF (10 ml); N-acetyl glycine amide (0.3222 g) and $Cs_2CO_3$ (0.9055 g) were added at room temperature and allowed to heat at 140° C. for 7 hrs. Progress of the reaction was monitored by TLC. Water was added to the reaction mixture then solid was thrown out. Solid was filtered off and dried in vacuum to form a light yellowish solid.

Step 4:
(Set up a SN RB flask equipped with Guard tube).
To 6 (1.2 g) dissolved in ethyl acetate (excess); 12 N HCl (catalytic amount) was added at 0° C. After the completion of the addition, compound was thrown out from ethyl acetate. Solid was filtered off and 40% EtOAc/hexane washes were given then completely dried on vacuum.

NMR and Molecular Mass Data
NMR and molecular mass data for Compounds III, V, VI, XI and II are detailed in Table 1 below.

TABLE 1

$^1$NMR and Mass (m/e) Data

| Structure | H NMR IN DMSO | MASS: m/e |
|---|---|---|
| Compound III | δ = 3.85 (s, 6H); 6.12 (s, 2H); 6.70 (s, 2H); 6.75 (s, 2H); 7.10 (d, 1H); 7.33 (d, 1H); 7.42 (s, 1H); 7.50 (d, 1H); 7.61 (d, 1H). | 352.05 |
| Compound V | δ = 3.82 (s, 3H); 3.89 (s, 3H); 6.06 (s, 2H); 6.49 (s, 1H); 6.88 (s, 1H); 7.03 (d, 1H); 7.05 (s, 1H); 7.36 (d, 1H); 7.40 (d, 1H); 7.43 (d, 1H); 11.56 (s, 1H). | 352.05 |
| Compound VI | δ = 3.82 (s, 3H); 6.10 (s, 2H); 6.51 (s, 1H); 6.87 (s, 1H); 7.8 (d, 2H); 7.53 (d, 1H); 7.48 (d, 1H); 7.12 (d, 2H); 7.02 (s, 1H); 11.6 (s, 1H). | 322.15 |
| Compound XI | δ = 3.80 (s, 3H); 3.86 (s, 3H); 6.73 (s, 1H); 6.82 (d, 1H); 7.12 (d, 1H); 7.16 (s, 1H); 7.19 (d, 1H); 7.21 (s, 1H); 7.51 (s, 1H), 7.57 (d, 1H). | 338, 340, 360, 378, 403, 419, 420, 444 |
| Compound II | δ = 1.05 (t, 3H); 1.78 (m, 2H); 3.85 (s, 6H); 4.05 (t, 2H); 6.50 (s, 1H); 6.85 (s, 1H); 7.05 (d, 2H); 7.45 (d, 2H); 7.75 (d, 2H); 7.02 (s, 1H); 11.65 (s, 1H) | 366.10 |

Example 1

Biological Activity

Pro-Drug Cytotoxicity in Wild-Type Cho Cells and Cho Cells Engineered to Express Cyp1A1 and CYP1B1 Enzymes Engineered CHO cells were used to demonstrate selective cell killing mediated by CYP1 expression. In the experiments described below, compounds were exposed to wild-type CHO cells engineered to express either CYP1A1 (CHO/CYP1A1) or CYP1B1 (CHO/CYP1B1) enzymes.

CHO cells: Chinese Hamster Ovary (CHO) DUKXB11 cells were grown under standard cell culture conditions in α-MEM supplemented with 10% FCS, 1 unit/ml each of hypoxanthine and thymidine, and penicillin (100 IU/ml) and streptomycin (100 μg/ml) according to literature methods (Ding S, et al., *Arch. Biochem. Biophys.*, 348: 403-410, 1997, the contents of which are incorporated herein by reference). Cells were grown at 37° C. in a humidified atmosphere plus 5% $CO_2$.

CHO/CYP1A1 and CHO/CYP1B1 cells: CHO cells containing recombinant CYP1A1 and recombinant CYP1B1 co-expressing P450 reductase, namely (CHO/CYP1A1) and (CHO/CYP1B1) respectively, were cultured using the standard culture medium for CHO cells supplemented with 0.4 mg/ml G418 disulfate salt and 0.3 μM methotrexate (Sigma/Aldrich Co., Gillingham, Dorset, UK) according to methods described in the literature (ibid.) Cells were grown at 37° C. in a humidified atmosphere plus 5% $CO_2$.

Recombinant CYP1A1 and CYP1B1 Expression
Dihydrofolate reductase (DHFR) gene amplification of either human cDNA CYP1A1 or cDNA CYP1B1 in CHO cells was used to achieve high levels of functional enzyme when co-expressed with human P450 reductase (ibid.; Ding S, et al., *Biochem J.*, 356(Pt 2): 613-9, 2001). Modified CYP1A1 or CYP1B1 cDNA was digested and ligated into to the mammalian expression vector pDHFR to generate the plasmids pDHFR/1A1 and pDHFR/1B1, respectively (ibid.) Cell culture and DNA transfection into CHO DUKXB11 was carried out according to methods described in the literature and transfected cells selected for the DHFR+ phenotype by growth in nucleoside deficient medium (ibid.) DHFR+ clones were pooled, and grown on increasing concentrations of MTX (0.02 to 0.1 μM) for amplification of transfected CYP1A1 or CYP1B1 cDNA. Cell clones that survived 0.1 mM MTX selection were isolated then further selected with 0.3 μM MTX. The resulting cell lines were analysed for CYP1A1 or CYP1B1 expression by immunoblotting. Cell lines expressing a high level of each enzyme were stably transfected with plasmid pcDNA/HR containing a full length human cytochrome P450 reductase (CPR) cDNA, and selected with G418 (0.8 mg/ml) and MTX (0.3 μM) according to methods described on the literature (ibid.) After isolation of resistant clones the concentration of G418 was reduced to 0.4 mg/ml and the homogeneity of the cell lines assured by repeated cloning. The CHO cell line transfected with the plasmid carrying cDNA CYP1A1 subsequently transfected with CPR cDNA was designated CHO/CYP1A1 and the CHO cell line transfected with the plasmid carrying cDNA CYP1B1 subsequently transfected with CPR cDNA was designated CHO/CYP1B1.

Immunochemical Detection of CYP1A1 and CYP1B1
Cells were harvested and lysed by sonication using standard methods in the literature (Ding S, et al., 1997, the contents of which are incorporated herein by reference). Proteins (typically 50 μg of lysate) were separated by SDS/PAGE, transferred to a nitrocellulose membrane and probed using standard methods (Paine M J, et al., *Arch. Biochem. Biophys.*, 328: 380-388, 1996, the contents of which are also incorporated herein by reference). Human CYP1A1 plus reductase Supersomes™, human CYP1A2 plus reductase Supersomes™ and CYP1B1 plus reductase Supersomes™ (BD Biosciences, Oxford, UK) were used as positive controls (typically 0.03 to 0.3 pmole) for immunochemical detection of enzyme expression in cell lines. A WB-1B1 primary antibody (dilution 1:1500, BD Biosciences, Oxford, UK) and an anti-CYP1A2 antibody which cross reacts with CYP1A1 (dilution 1:2000, Cancer Research Technology, London, UK) were used to detect CYP1B1 and CYP1A1 expression, respectively. The secondary antibody was goat anti-rabbit IgG used at a 1:500 dilution. Immunoblots were developed using the Enhanced Chemiluminescence (ECL) Western-blot detection kit (GE Healthcare Life Sciences, Amersham, Buckinghamshire, UK).

Western-Blot Characterization of CYP1A1 and CYP1b1 Expression in Cells

Figure 1A:
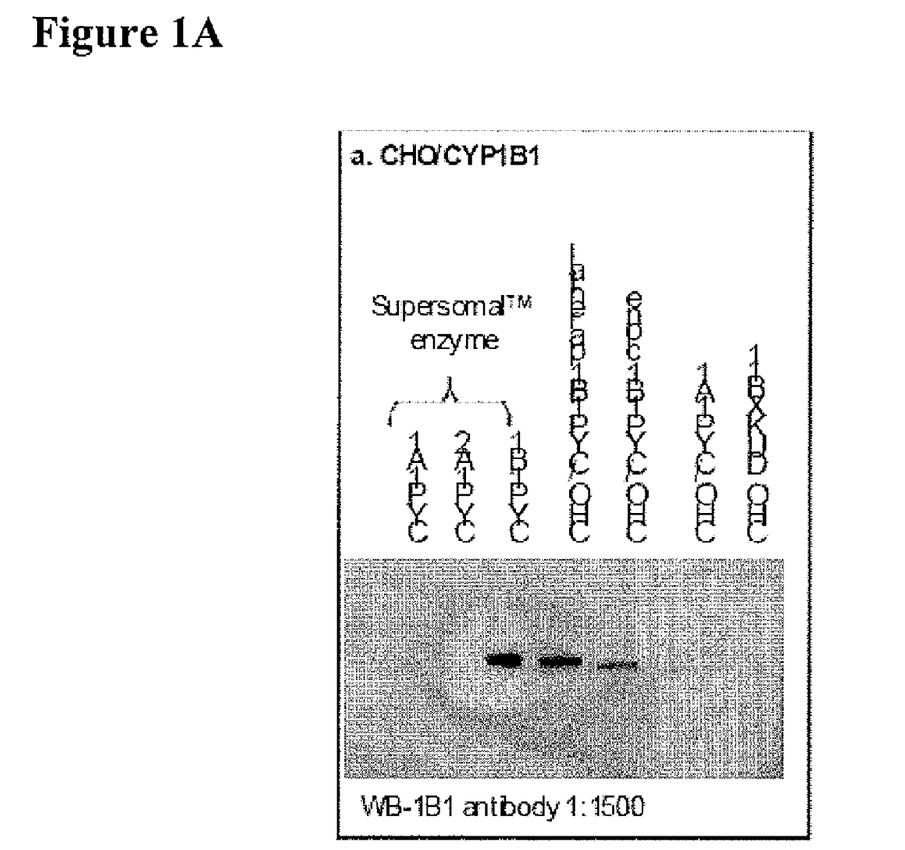
FIGS. 1a and 1b are images of Western-blots showing the detection of CYP1B1 expression in the transfected CHO/CYP1B1 cell line (FIG. 1a) and CYP1A1 expression in the transfected CHO/CYP1A1 cell line (FIG. 1b).
Figure 1B:
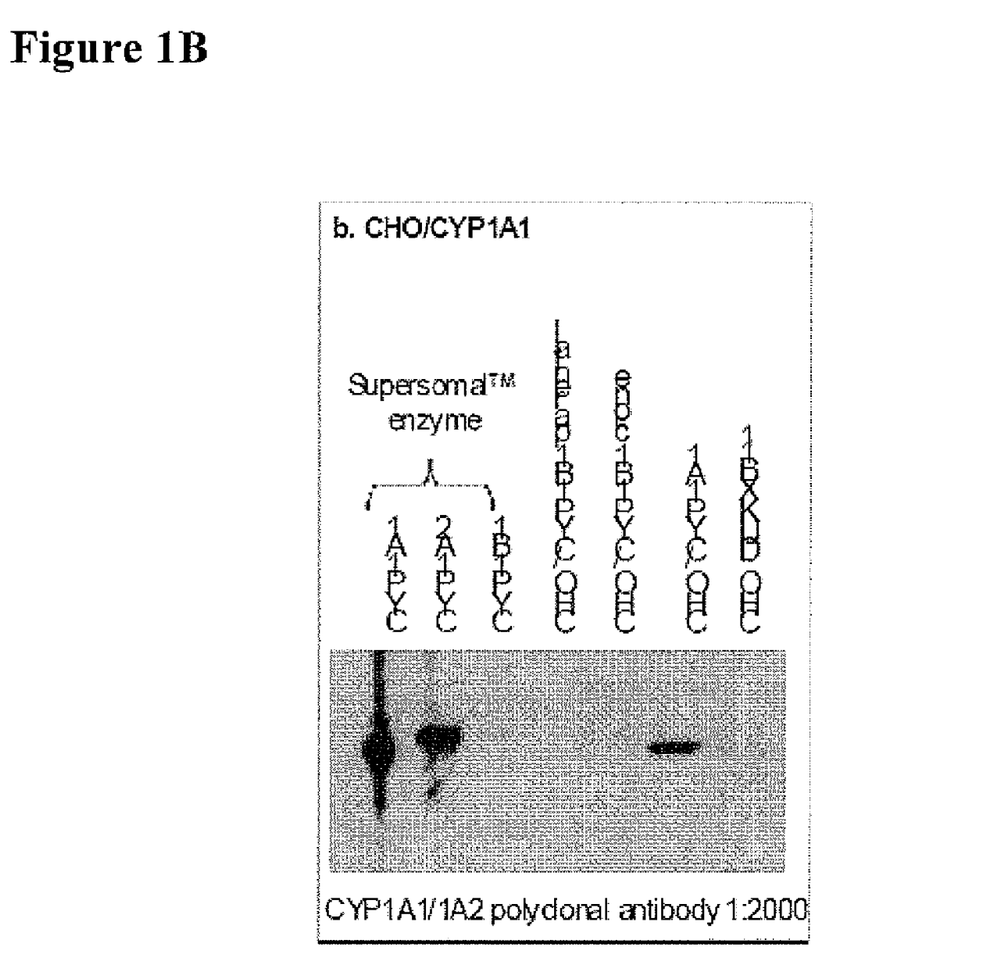

FIG. 1a of the accompanying drawings is a typical western-blot showing the detection of CYP1B1 protein expression in lysate from the CHO/CYP1B1 cell line which is detectable in neither the untransfected CHO DUKXB11 cells nor the CHO/CYP1A1 cell line. The band corresponds to a molecular weight of 56 kDa and matches the band for human CYP1B1 Supersomal™ enzyme. FIG. 1b is a typical western-blot showing the detection of CYP1A1 protein expression in lysate from the CHO/CYP1A1 cell line which is detectable in neither the untransfected CHO DUKXB11 cells nor the CHO/CYP1B1 cell line. The band corresponds to a molecular weight of 60 kDa and matches the band for human CYP1A1 Supersomal™ enzyme detected by the cross reactivity of the anti-CYP1A2 antibody.

Functional CYP1 Activity

The EROD assay is widely used to confirm functional CYP1 activity (Chang T K and Waxman D J, "Enzymatic Analysis of cDNA-Expressed Human CYP1A1, CYP1A2, and CYP1B1 with 7-Ethoxyresorufin as Substrate", *Methods Mol. Biol.*, 320: 85-90, 2006, the contents of which are incorporated herein by reference). The assay determines O-dealkylation of 7-ethoxyresorufin by CYP1A1, CYP1A2, and CYPB1 to generate the enzymatic product resorufin, which is monitored continuously by fluorescence at 580 nm. The EROD assay and selective and non-selective CYP1 inhibitors were used to confirm that the CHO cell lines referred to above were expressing the expected CYP1 enzymes in a functional form.

In the absence of inhibitors, CHO/CYP1A1 and CHO/CYP1B1 (but not wild-type CHO cells) converted 7-ethoxyresorufin to resorufin, thereby confirming functional CYP1 expression in these cells (see Table 2 below).

As expected, addition of the broad-spectrum CYP1 inhibitor, α-naphthoflavone, abolished activity in both CYP1 expressing cell lines (Table 2). The selective inhibitor, Tetramethoxystilbene, is 30 fold selective for CYP1B1 over CYP1A1 (Chun Y J, Kim S, Kim D, Lee S K and Guengerich F P, "A New Selective and Potent Inhibitor of Human Cytochrome P450 1B1 and its Application to Antimutagenesis", *Cancer Res* 61(22): 8164-70, 2001). Tetramethoxystilbene abolished activity at high concentrations in both CYP1 expressing cell lines and preferentially decreased activity in CYP1B1 expressing cells (compared with CYP1A1 expressing cells) cells at lower concentrations (Table 2).

TABLE 2

Specific CYP1 activity in CHO cells (pmol resorufin min$^{-1}$ mg protein$^{-1}$)

| Inhibitor | CHO | CHO/CYP1A1 | CHO/CYP1B1 |
|---|---|---|---|
|  | nd | 29 ± 4 | 19 ± 3 |
| α-naphthoflavone (10 μmol) | nd | nd | nd |
| Tetramethoxystilbene (5 μmol) | nd | nd | nd |
| Tetramethoxystilbene (10 nM) | nd | 26 ± 4 | 5 ± 2 |

These results provide independent confirmation that the CYP1A1 and CYP1B1 expression levels are as expected.

Determining Cytotoxicity IC$_{50}$ Values in CHO, CHO/CYP1A1 and CHO/CYP1B1 Cell Lines A single cell suspension of CHO, CHO/CYP1A1 or CHO/CYP1B1 in 100 μl of the required cell culture medium was seeded onto 96-well plates at a cell density of 1500 cells per well and placed in an incubator for 24 h at 37° C. The stock solution of test compound in DMSO was then added to give a concentration range of 100, 30, 10, 3, 1, 0.3, 0.1, 0.03, 0.01, 0.003, 0.001, 0 μM. The final concentration of DMSO 0.2% was found not to affect the growth characteristics of the various CHO cell lines. The cells were incubated with the test compound for 96 h after which all the medium was aspirated and replaced with 100 μl of fresh medium to compensate for the loss of medium due to evaporation. The cells were incubated with 20 μl of the MTS assay reagent for 1.5 h and the absorbance per well at 510 nm measured using a plate reader. The mean absorbance and standard deviation for each test compound concentration was calculated versus a series of controls including (a) cells plus medium, (b) cell plus medium containing DMSO 0.2%, (c) medium alone, and (d) medium containing DMSO 0.2% and a range of test compound concentrations from 0 to 100 μM. The cytotoxicity IC$_{50}$ value was calculated from the plot of the percentage cell growth (where 100% cell growth corresponds to untreated control cells) versus test compound concentration.

Cytotoxicity IC$_{50}$ values are defined herein as the concentration of compound which kills 50% of cells and fold selectivity is calculated by dividing the IC$_{50}$ in non-CYP1 expressing cells with the IC$_{50}$ in CYP1A1 or CYP1B1 expressing cells.

Promega™ CellTiter 96® Aqueous Non-Radioactive Cell Proliferation (MTS) Assay

The MTS assay is a homogeneous, colorimetric method for determining the number of viable cells in proliferation, cytotoxicity or chemosensitivity assays (Cali J J, et al., "Luminescence-Based Methods and Probes for Measuring Cytochrome P450 Activity", pp. 1-29. Promega Corporation, United States, 2004, the contents of which are incorporated herein by reference). The assay is composed of solutions of tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine methosulfate) PMS. MTS is bioreduced by cells into a formazan product that is soluble in tissue culture medium. The absorbance of the formazan product at 510 nm can be directly measured from 96-well assay plates. The quantity of formazan product as measured by the amount of absorbance at 490 or 510 nm is directly proportional to the number of living cells in culture.

The compounds of the invention mentioned Table 3 below exhibit no (or negligible) toxicity to wild-type CHO cells, confirming that (in the absence of CYP1 expression) the compounds are non-toxic or substantially non-toxic pro-drugs. The mechanism of activation of the pro-drugs can be deduced from their activity against the two CYP1 expressing cell lines: CHO/CYP1A1 and CHO/CYP1B1. For example, Compound V, Compound VI and Compound II are non toxic to both wild-type and CYP1A1 expressing CHO cells, but strongly inhibit proliferation of CHO/CYP1B1 cells with $IC_{50}$ values ranging from 80 nM (Compound V) to 500 nM (Compound VI). Compounds II, V and VI are therefore CYP1B1 activated pro-drugs. Crucially, these CYP1B1 selective prodrugs are 200-1250 fold more toxic to CYP1B1 expressing cells than non-CYP1B1 expressing cells (Table 3). Compound III is active against CHO/CYP1A1 and CHO/CYP1B1 cells, implying that it is activated by both CYP1A1 and CYP1B1 enzymes (Table 2).

TABLE 3

Prodrug Activity in CHO, CHO/CYP1A1 and CHO/CYP1B1 Cells

| Compound‡ | CHO $IC_{50}$ μM | CHO/CYP1A1 $IC_{50}$ μM | CHO/CYP1B1 $IC_{50}$ μM |
|---|---|---|---|
| III | 6.11 ± 0.34 | 0.95 ± 0.35 | 0.04 ± 0.03 |
| V | >100 | >100 | 0.08 ± 0.01 |
| VI | >100 | >100 | 0.5 ± 0.1 |
| II | >50 | >50 | 0.09 ± 0.05 |

‡Compound nos. refer to the compounds of formulae II to VI above.

Example 2

Metabolite Activity

In order to demonstrate one mechanism of action of the above described compounds, Compound V and its putative metabolite Compound XI were tested in the Cerep DiversitySExpress Kinase screen (Thierry Jolas, Study No. 13991, In vitro Pharmacology: Diversity ExpresSKinase Profile, which is incorporated herein by reference).

Kinase Screening

Kinase screening was performed by Cerep Laboratories (Celle l'Evescault, France). Compounds were screened in duplicate at a single concentration (10 μM). The results, set forth in Table 4 below, are expressed as percent inhibition of control specific activity:

{100−[(measured specific activity/control specific activity)×100]} obtained in the presence of Compound XI and Compound V. ATP concentrations correspond to the ATP Km value for each individual kinase (Cerep, private communication). In each experiment, a reference compound was tested concurrently with Compound XI and Compound V in order to assess the assay reliability. $IC_{50}$ values for the reference compounds were within accepted limits (±0.5 log units) of the historic average.

Both the parent compound (Compound V) and the metabolite (Compound XI) were tested at 10 μM. The results show that Compound XI (but not Compound V) inhibits a range of kinases known to play a key role in cancer tumourigenesis (see Table 4 below).

TABLE 4

Kinase Activity of Compound V and Its Putative Metabolite: Compound XI

| | | | % Inhibition of Control | |
|---|---|---|---|---|
| Kinase | Group | Family | Compound V (10 μM) | Compound XI (10 μM) |
| C-Met (HGFR) | TK | Met | −5% | 58% |
| CSK | TK | Csk | 4% | 98% |
| FGFR2 | TK | FGFR | 13% | 98% |
| FGFR4 | TK | FGFR | −3% | 85% |
| FLT-1 | TK | VEGFR | 11% | 98% |
| FLT-3 | TK | PDGFR | 21% | 93% |
| Fyn | TK | Src | 25% | 100% |
| KDR (VEGFR2) | TK | VEGFR | 19% | 96% |
| Lyn | TK | Src | −1% | 99% |
| PDGFRβ | TK | PDGFR | 7% | 91% |

Example 3

Cytochrome P450 Metabolism

As mentioned above, a feature of the compounds of the invention is their metabolism by CYP1B1 which is expressed at high frequency in a wide range of human cancers of different histogenetic types, but not in normal tissues. In order to demonstrate that the compounds of the invention are not substrates for cytochrome P450 enzymes present in normal tissue, Compounds V and II were assayed in CYP phenotyping assays at Cerep (Mao Boryeu, Study No. 13652, ADME-Tox CYP Phenotyping, which is incorporated herein by reference). Compounds V and II were exposed to a panel of six CYPs (see Table 5 below). The results show that neither compound is significantly metabolised by any of the major xenobiotic metabolizing CYP enzymes.

TABLE 5

Metabolic Stability in the presence of CYP enzymes

| CYP Enzyme | Compound V Mean Parent Remaining (%) | Compound II Mean Parent Remaining (%) | Reference Compound | % Reference Compound Remaining |
|---|---|---|---|---|
| CYP1A2 (40 pm/mL) | 71 | 69 | Ethoxyresorufin | 0 |
| CYP2C9 (10 pm/mL | 109 | 130 | Diclofenec | 0 |
| CYP2C19 (10 pm/mL) | 111 | 127 | Imipramine | 20 |
| CYP2D6 (10 pm/mL) | 100 | 127 | Imipramine | 3 |
| CYP3A4 (10 pm/mL) | 93 | 122 | Terfenadine | 14 |
| CYP3A5 (10 pm/mL) | 87 | 126 | Midazolam | 1 |

Methods: Cytochrome P450 Metabolism

CYP metabolism studies were performed by Cerep Laboratories (Redmond, Wash., USA). Compounds were screened in duplicate at 1 μM in the presence of CYP enzyme, NADP (1.3 mM), D-Glucose-6-phosphate (3.3 mM) and Glucose-6-phosphate dehydrogenase. Following incubation at 0 and 60 minutes, parent compound levels were determined using standard HPLC/MS/MS procedures. The results are expressed as percent parent compound remaining after 60 minutes.

Example 4

Biological Activity In Vivo

A xenograft study was performed to demonstrate the efficacy of the candidate drugs in an in vivo setting. The study compared the efficacy of Compound II with a vehicle control in UTSCC-14 xenograft tumours at three different dose levels.

Forty female nu/nu mice (7-9 wks old, weight 20-25 grams) were implanted sc with 2e6 UTSCC-14 cells and randomized 10 days later into four groups of 9 mice (Table 1) with an approximate tumour volume of 100-150 mm-3. All groups were dosed daily ip for 29 days. On day 40 tumours were excised and weighed.

The UTSCC-14 cells used in the experiment were sourced from Professor Reidar Grénman's laboratory at the University of Turku, Department of Head and Neck Surgery, Turku University, Turku, Finland) and taken from a grade II primary tumour from the tongue of a male head and neck cancer patient.

TABLE 6

| | |
|---|---|
| Group 1 | Vehicle control (50% DMSO in water) i.p. (5 ul/g) |
| Group 2 | Compound II (in 50% DMSO in water*) 7 mg/kg i.p. (5 ul/g) |
| Group 3 | Compound II (in 50% DMSO in water*) 20 mg/kg i.p. (5 ul/g) |
| Group 4 | Compound II (in 50% DMSO in water*) 50 mg/kg i.p. (5 ul/g) |

The study timeline is outlined in Table 7.

| | |
|---|---|
| Day 0 | Implant cells into mice (40 mice, sc flank), 2e6 cells/mouse |
| Day 10 | Measure tumours, weigh mice, randomize into four groups |
| Day 10 | Begin dosing |
| Day 39 | Complete dosing |
| Day 40 | Excise and weigh tumours (24 hours after last dose) |

Compound II was dissolved/suspended in 100% cell culture grade DMSO at 40 mg/ml, before dilution with ddH20 immediately prior to dosing to make a stock 50% DMSO/Water solution. This stock solution was used to prepare all doses by dilution with 50% DMSO/Water to achieve the required concentration.

Figure 2:
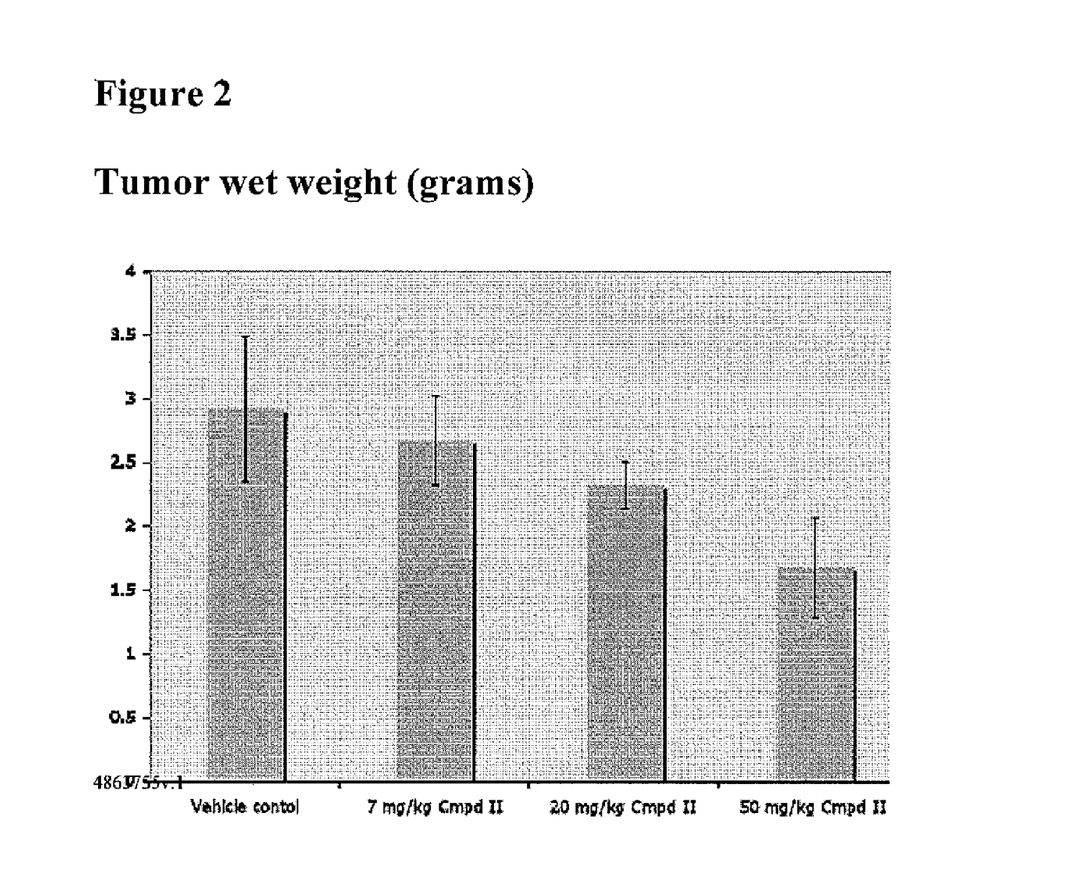
FIG. 2 shows a graph of the weight (in grams) of tumours as a result of activity of compounds according to the present invention.

FIG. 2 compares the weight in grams of tumours excised on day 40 of the study. The graph shows a dose dependent reduction in wet tumour weight at the end of the study. These results demonstrate activity in an in vivo model using cells taken directly from a cancer patient. The study provides evidence that Compound II (and related compounds described here) are useful in the development of novel cancer therapies.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A compound of formula (I):

(I)

or a pharmaceutically acceptable salt thereof, wherein:
$R^1$, $R^2$ and $R^3$ are independently H or lower alkyl;

$R^4$, $R^5$, $R^6$, $R^7$ and $R^8$ are independently H, halo, lower alkyl or —O-lower alkyl, provided that at least one is —O-lower alkyl; or at least one pair of $R^4$ to $R^8$, the members of which pair are adjacent to one another on the ring, are conjoined to form —O—$(CR^{14}R^{15})_n$—O—, where n is 1 or 2 and $R^{14}$ and $R^{15}$ are independently H or lower alkyl, and the remainder of $R^4$ to $R^8$ are independently H, halo, lower alkyl or —O-lower alkyl; and $R^9$, $R^{10}$, $R^{11}$, $R^{12}$ and $R^{13}$ are independently H, halo, lower alkyl or —O— lower alkyl, provided that at least one pair of $R^9$ to $R^{13}$, the members of which pair are adjacent to one another on the ring, are conjoined to form —O—$(CR^{16}R^{17})_m$—O—, where m is 1 or 2 and $R^{16}$ and $R^{17}$ are independently H or lower alkyl, and the remainder of $R^9$ to $R^{13}$ are independently H, halo, lower alkyl or —O-lower alkyl.

2. The compound as claimed in claim 1, wherein $R^6$ and $R^{11}$ are not both —OMe.

3. The compound as claimed in claim 1, wherein $R^9$, $R^{12}$ and $R^{13}$ are independently H, halo or lower alkyl, and $R^{10}$ and $R^{11}$ are conjoined to form —O—$C(R^{16}R^{17})_m$—O—, where m is preferably 1.

4. The compound as claimed in claim 1, wherein one of $R^9$ to R13 is —O—$R^{18}$, $R^{18}$ is lower alkyl.

5. The compound as claimed in claim 1, wherein at least two of $R^4$, $R^5$, $R^6$, $R^7$ and $R^8$ are —O-lower alkyl.

6. The compound as claimed in claim 1, wherein $R^6$ is —O—$R^{19}$, $R^{19}$ is lower alkyl.

7. The compound as claimed in claim 1, wherein said compound is:

(III)

(V)

(VI)

8. A pharmaceutical composition comprising one or more compounds of claim 1, together with one or more pharmaceutically acceptable excipients.

* * * * *

UNITED STATES PATENT AND TRADEMARK OFFICE
CERTIFICATE OF CORRECTION

PATENT NO. : 8,236,827 B2  
APPLICATION NO. : 12/478587  
DATED : August 7, 2012  
INVENTOR(S) : Gerard A. Potter et al.

Page 1 of 1

It is certified that error appears in the above-identified patent and that said Letters Patent is hereby corrected as shown below:

On the Title page, the following section should be added:

(30)   Foreign Application Priority Data

Jun. 4, 2008   (GB) .................0810228.7

Signed and Sealed this  
Ninth Day of April, 2013

Teresa Stanek Rea  
*Acting Director of the United States Patent and Trademark Office*